United States Patent [19]

Keen et al.

[11] Patent Number: 4,760,200

[45] Date of Patent: Jul. 26, 1988

[54] PROCESS FOR THE PRODUCTION OF ALKYLENE GLYCOLS

[75] Inventors: Brian T. Keen; John H. Robson, both of Charleston; George E. Keller, II, South Charleston, all of W. Va.

[73] Assignee: Union Carbide Corporation, Danbury, Conn.

[21] Appl. No.: 815,008

[22] Filed: Dec. 31, 1985

[51] Int. Cl.$^4$ .................... C07C 29/10; C07C 31/20
[52] U.S. Cl. .................... 568/867; 568/811; 568/833; 568/857
[58] Field of Search ............... 568/867, 811, 833, 857

[56] References Cited

U.S. PATENT DOCUMENTS

| | | | |
|---|---|---|---|
| 2,141,443 | 12/1938 | Stanley et al. | 568/867 |
| 3,933,923 | 1/1976 | Osberghaus et al. | 568/867 |
| 4,277,632 | 7/1981 | Kumazawa et al. | 568/867 |
| 4,390,738 | 6/1983 | Waddan et al. | 568/867 |
| 4,551,566 | 11/1985 | Robson et al. | 568/867 |
| 4,560,813 | 12/1985 | Collier | 568/867 |
| 4,564,715 | 1/1986 | Briggs et al. | 568/867 |
| 4,571,440 | 2/1986 | Keen et al. | 568/867 |

FOREIGN PATENT DOCUMENTS

| | | | |
|---|---|---|---|
| 2023601 | 1/1980 | United Kingdom | 568/867 |
| 2083026 | 3/1982 | United Kingdom | 568/867 |

*Primary Examiner*—J. E. Evans
*Attorney, Agent, or Firm*—Norman L. Balmer

[57] ABSTRACT

The process for the liquid-phase hydration of a vicinal alkylene oxide(s) to the corresponding alkylene glycol(s) comprising carrying out such hydration in an aqueous medium containing a water miscible alkylene glycol ether co-solvent.

9 Claims, No Drawings

PROCESS FOR THE PRODUCTION OF ALKYLENE GLYCOLS

This invention relates to processes for the hydrolysis of vicinal alkylene oxides to the corresponding alkylene glycols. More specifically, it relates to processes for the production of alkylene glycols by the hydration of alkylene oxides in an aqueous liquid menstruum containing a water miscible alkylene glycol ether.

BACKGROUND OF THE INVENTION

Alkylene oxides, for example ethylene oxide, propylene oxide and butylene oxide, have been subjected to liquid phase hydration to produce the corresponding alkylene glycols. Commercially, in the production of ethylene glycol from ethylene oxide large molar excesses of water are used (See: Kirk-Othmer: Encyclopedia of Chemical Technology Volume 11, Third Edition, Page 939, (1980)). It has been reported that the presence of large quantities of water in the reaction system are necessary if the yield to the desired monoalkylene glycol is to be great enough to be commercially viable and minimize the production of by products such as diglycols and triglycols. Accordingly, the commercial practice has generally involved the hydration of an alkylene oxide at a temperature of about 100° C. to about 200° C. in the presence of a large molar excess of water, for example, in excess of 15 moles of water per mole of alkylene oxide, when the corresponding monoalkylene glycol is to be produced. Unfortunately, the use of such large excesses of water presents significant energy and equipment requirements for its removal.

Since the selectivity of the hydration process to monoglycol, e.g., ethylene glycol, propylene glycol or butylene glycol, is dependent on the by products formed, it would be desirable to provide a process that would increase the selectivity of the hydration process to monoglycol products. In addition, any process which would favorably decrease the relative amount of water employed to alkylene oxide hydrated while not increasing, or preferably decreasing, the by products formed would be advantageous. Thus, the energy and equipment requirements would necessarily be less for separation and purification processes relating to the removal and recovery of the monoglycol from water and by products.

As a result of the desire to improve the hydration process, both in terms of selectivity to desired product and the energy requirements to effect the purification and recovery of the desired product, several processes have been suggested which provide for the hydration of an alkylene oxide in the presence of a specific catalyst such that the ratio of water to alkylene oxide may be lowered and such that the selectivity to monoglycol product is maintained or enhanced.

Numerous catalysts have been suggested for use in the hydration of alkylene oxides, including the use of acid catalysts such as: alkyl sulfonic acid ion exchange resins (U.S. Pat. No. 4,165,440); carboxylic acids and halogen acids (U.S. Pat. No. 4,112,054); strong acid cation exchange resins (U.S. Pat. No. 4,107,221); aliphatic monocarboxylic and/or polycarboxylic acids (U.S. Pat. No. 3,933,923); cationic exchange resins (U.S. Pat. No. 3,062,889); acidic zeolites (U.S. Pat. No. 3,028,434); sulfur dioxide (U.S. Pat. No. 2,807,651); $Ca_3(PO_4)_2$ (U S. Pat. No. 2,770,656); high melting polyvalent metal fluorides (U.S. Pat. No. 2,547,766); trihalogen acetic acid (U.S. Pat. No. 2,472,417); and copper-promoted aluminum phosphate (U.S. Pat. No. 4,014,945).

In addition to the acid catalysts, numerous catalysts have been suggested for the hydration of alkylene oxides in the presence of carbon dioxide. These include alkali metal halides, such as chlorides, bromides and iodides, quaternary ammonium halides such as tetramethyl ammonium iodide and tetramethyl ammonium bromide (British Pat. No. 1,177,877); organic tertiary amines such as triethylamine and pyridine (German published patent application No. 2,615,595, Oct. 14, 1976, and U.S. Pat. No. 4,307,256, issued Dec. 22, 1981); quaternary phosphonium salts (U.S. Pat. No. 4,160,116, issued July 3, 1979); and chlorine or iodine type anion exchange resins (Japanese Kokai No. 57/139,026, published Aug. 27, 1982); and partially amine neutralized sulfonic acid catalyst, e.g., partially amine neutralized sulfonic acid resin (U.S. Pat. No. 4,393,254, issued July 12, 1983).

Although a review of the results reported in the patent literature would suggest that the above described catalysts have provided commercially acceptable results, that is, a high selectivity to the monoglycol product and a decrease in the requirement for large molar excess of water, these catalysts have not been commercially employed for several reasons. For example, alkali metal halides tend to corrode the reaction system at the temperatures employed for the hydration of alkylene oxides. The relatively low solubility of alkali metal halides and quaternary ammonium halides in alkylene glycol restricts their use as hydration catalysts since they are likely to precipitate within the reaction system during the course of the hydration reaction and can result in problems associated with cleaning the reaction system. In addition, some catalysts, such as tertiary amines, have certain chemical and physical properties which prevent their ready use as hydration catalysts. For example, tertiary amines have a strong pungent odor which is not desirable in manufacturing and can detract from the quality of the end product.

U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

Japanese Kokai No. JA 56/92228, published July 25, 1981, is directed to processes for producing highly pure alkylene glycols. The disclosure is directed to a distillation procedure for recovery of a molybdenum and/or tungsten containing catalyst from an alkylene oxide hydrolysis process in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples.

Patent applications Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble metavanadate. Hence, lower water to alkylene oxide ratios can be employed using the disclosed process with attractive selectivities to the monoglycol products. The counter ion to the metavanadate is selected to provide a water-soluble metavanadate salt under the reaction conditions employed and alkali metals, alkaline earth metals, quaternary ammonium, ammonium, copper, zinc, and iron are suggested cations. It is also disclosed that the metavanadate may be introduced into the reaction system in the salt form or on a support such as silica, alumina, zeolites and clay. Since the metavanadate ion is water-soluble, it can be lost from the reaction system and means must be provided to recover it from the effluent from the reaction zone.

Unfortunately, insoluble salts of vanadate anion, such as calcium vanadate, as well as insoluble molybdate and other metalate salts do not appear to provide the selectivity toward the monoglycol products which is achievable with the water-soluble metalates. The problems with the recovery of the metalate are significant factors in considering the use of the technology on a commercial scale.

Japanese Kokai No. JA 57/139,026, published Aug. 27, 1982, discloses a process for the hydrolysis of alkylene oxides in the presence of carbon dioxide and a halogen type anion exchange resin as a catalyst. The exemplified catalyst is a chlorine type anion exchange resin (Dowex MSA-1(TM), a product of the Dow Chemical Company) and a similar iodine-type anion exchange resin. At a mole ratio of alkylene oxide to water of about 0.66, the selectivity to monoethylene glycol was reported to be 91.0 percent using the chlorine type anion exchange resin and 89.6 percent using the iodine-type anion exchange resin. In the absence of carbon dioxide, the application disclosed that a selectivity to the monoethylene glycol of 34.8 percent was obtained and an unpleasant smell was noted in the product. In the absence of any anion exchange resin and in the presence of carbon dioxide, the selectivity to monoethylene glycol was reported to be 37.5 percent. All of the examples were conducted in an autoclave immersed in an oil bath at a temperature of 150° C. The disclosure reports that the maximum reaction liquid temperature was 130° C. and the reaction was carried out for 90 minutes. While the application did not specifically indicate the source of the unpleasant smell which originated in the comparative example where the carbon dioxide atmosphere was not employed, it could have been the result of degradation of the anion exchange resin.

Copending U.S. Patent application Ser. No. 594,385 of J. R. Briggs and J. H. Robson, is directed to processes for the hydrolysis of alkylene oxide with enhanced selectivities to monoalkylene glycols using a reaction menstruum comprising an agueous phase, a water-immiscible liquid phase and a metalate anion-containing material wherein the concentration of the metalate anion-containing material in the water-immiscible phase is greater than that in the aqueous phase.

SUMMARY OF THE INVENTION

This invention relates to processes for the production of the corresponding monoalkylene glycol by the hydration in a liquid phase of an alkylene oxide having the general formula:

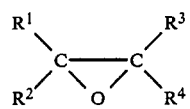

$R^1$, $R^2$, $R^3$ and $R^4$ being as hereinafter set forth, in an aqueous liquid menstruum containing a water miscible alkylene glycol ether.

The processes of this invention provide enhanced selectivity to monoalkylene glycol. For instance, the selectivities achievable using this invention are greater than those obtained under common conditions but not employing the solvent component of the liquid menstruum.

DETAILED DESCRIPTION OF THE INVENTION

This invention relates to processes for the production of monoalkylene glycols by the reaction of water with vicinal alkylene oxide having the general formula

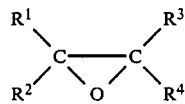

wherein $R^1$, $R^2$, $R^3$ and $R^4$ each designate a hydrogen atom, an alkyl group having between 1 and about 10 carbon atoms, an aryl group having at least 6 carbon atoms (e.g., monocyclic or bicyclic aryl), an alkenyl group having 2 or 3 carbon atoms or a cycloalkyl group having 3 to 6 carbon atoms. Representative of the alkylene oxides which may be employed in the instant invention are ethylene oxide, propylene oxide, butylene oxide, including isobutylene oxide, 1,2-butylene oxide and 2,3-butylene oxide, pentylene oxide, cyclohexene oxide, styrene oxide, and the like. Preferably, the alkylene oxide is an aliphatic alkylene oxide such as ethylene oxide and propylene oxide.

The source of the alkylene oxide is not generally important, and alkylene oxide formed by most any process may be employed in the instant invention. For example, if ethylene oxide is the selected alkylene oxide it may be formed by the catalytic oxidation of ethylene with molecular oxygen or an oxygen-containing gas in the presence of a silver catalyst. Such a process for forming the ethylene oxide employed herein is particularly desirable since substantially pure ethylene oxide may be obtained.

The process also employs water as a reagent for the formation of the corresponding alkylene glycol. The source of the water is not important. Demineralized water obtained by, for example, ion exchange treatment, or other water of sufficient purity is usable in hydration processes. The amount of water to be used, relative to a mole of alkylene oxide, is generally between about 1 and about 40 moles, preferably up to about 30 moles, say, between about 1 and 30 moles and preferably between about 1 and 20 moles, and about 1 to about 10 moles if reducing energy and equipment costs for glycol-water separation is a primary objective. Although the molar ratio of water required for hydrolysis to alkylene oxide may be decreased below about 5 moles of water per mole of alkylene oxide, it is generally desirable to maintain at least a slight molar excess of water over the stoichiometric amount of water to ensure a higher selectivity of alkylene oxide to the monoalkylene glycol product.

The process further employs an organic co-solvent which is a water miscible alkylene glycol ether. This co-solvent should generally be present in amounts from about 5% to 85%, preferably 15% to 75% and most preferably 30% to 60% based upon the weight of total solvent employed. Preferred co-solvents are alkylene glycol ethers of the general formula

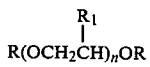

wherein R is $C_1$–$C_4$ alkyl, most preferably $CH_3$, $R_1$ is H or $C_1$–$C_4$ alkyl and n is a whole number ranging from 1 to about 10. The most preferred solvent is 1,2-dimethoxyethane (glyme).

The present process may or may not employ a catalyst. As shown by the references previously discussed, catalysts for the production of glycols through the hydrolysis of alkylene oxides are well known. If a catalyzed reaction is to be employed, the catalyst may be a soluble metalate anion, such as sodium molybdate, potassium molybdate and lithium molybdate, as disclosed in co-pending U.S. Serial No. 783,187, filed Oct. 2, 1985, the disclosure of which is hereby incorporated by reference. Also useful are alkyl ammonium molybdates, vanadates and tungstates as well as alkali metal vanadates and tungstates.

The catalyst may also be provided through use of catalyst-impregnated ion exchange resins, such as those disclosed in U.S. Ser. No. 594,268, filed March 28, 1984, the disclosure of which is hereby incorporated by reference. This process involves the contacting of the alkylene oxide and water with a metalate anion which is in association with electropositive complexing sites on a solid substrate. The metalates are characterized by an anionic structure containing at least one polyvalent metal atom, M, having a positive functional oxidation state, e.g., often an oxidation state of at least +3, usually +4 to +7, and at least one oxygen ligand which is conventionally characterized as a double-bonded oxygen atom. The metalate anion can be illustrated by the following formula:

wherein q is the negative charge of the anion, which is usually between −1 and −4, A is one or more substituents to fill the remaining valencies (m) of M, and may be the same or different, and may be, for instance, double-bonded oxygen; halogen (e.g., chlorine, fluorine, iodine); —O— or —S— wherein the remaining valency of the oxygen or sulfur atom is in free ionic form or is bonded to a metal atom (as in a bimetal or polymetal containing metalate) or a counter ion, e.g., alkali metal, alkaline earth metal, ammonium, phosphonium and the like cations; or an organic radical, e.g., alkyl, aryl, acyl, alkoxy, amino, phosphino, etc. of 1 to about 12 carbons; and the like. Most commonly A is —O— or ═O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals may also find application. Representative metalate anions which are especially useful include molybdate, tungstate, metavanadate, hydrogen pyrovanadate and pyrovanadate; although because of the complex chemistry associated with many metalate anions, the precise structure of the operative specie or species may be different. Frequently, the metalate anion is an anion conventionally characterized by a formula such as $[MoO_4]^{2-}$, $[VO_3]^-$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the added metalate anion) appear to exhibit less, if any, activity for enhancing selectivity.

However, in an aspect of the invention, the metal for the metalate anion is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as rhenate anion under the same conditions. Also, it is frequently the case that the metal as the metalate has an electrophilicity with respect to ethylene oxide greater than that exhibited by vanadium in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by the rhenate anion, then the metal as the metalate is probably less nucleophilic than rhenium in rhenate with respect to ethylene oxide. If the production of diethylene glycol and polyethylene glycol is greater than that provided with orthovanadate, regardless of the rate of formation of glycols, then the metal as the metalate is probably less electrophilic than orthovanadate with respect to ethylene oxide.

Because the selectivity enhancing metalate anions enhance the selectivity of the hydrolysis to the monoalkylene glycol product, it is believed that an interaction or even chemical reaction occurs between the metalate anion and the alkylene oxide. See, for example, copending U.S. Ser. No. 594,264, herein incorporated by reference. Any intermediate species formed between the metalate anion and alkylene oxide is believed to hydrolyze more rapidly to alkylene glycol than the rate at which it is formed. Thus, in the presence of water, the chemical determination of any intermediate species through techniques such as nuclear magnetic spectroscopy, is not presently feasible. Without being limited to theory, it is believed that advantageous metalate anions are those that are capable of interacting or reacting with alkylene oxide.

The electropositive complexing sites for association with metalate anion are on a water-insoluble support which may be organic or inorganic, i.e., the support is solid under the conditions of the reaction. The electropositive complexing sites and the water-insoluble support are substantially non-reactive with water, alkylene oxide and alkylene glycol.

The preferred electropositive complexing sites and the water-insoluble supports are those whose degradation products do not adversely affect the quality of the alkylene glycol product or can be facilely removed from the alkylene glycol product.

Typical electropositive complexing moieties can contain strongly electropositive complexing groups such as quaternary ammonium groups, quaternary phosphonium groups, sulfonium groups, or arsonium groups or moderately electropositive complexing groups such as protonated tertiary amines and protonated tertiary phosphines. Because of the stability and availability of quaternary ammonium and tertiary amine groups, they are generally preferred.

Suitable electropositive complexing groups include those having the general formula:

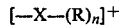

wherein X is nitrogen, phosphorous, sulfur, or arsenic, or tin bonded directly or indirectly to the support; and R may be the same or different and is hydrogen, monocyclic aryl or aralkyl of 6 to 8 carbon atoms, monocyclic alkaryl of 7 to 9 carbon atoms, or alkyl or alkoxy of 1 to about 6 carbon atoms, and R may be substituted with groups which are substantially non-reactive with alkylene oxide, alkylene glycol, or water, e.g., hydroxy groups such as hydroxyalkyl substituents, haloalkyl substituents, silyl substituents, siloxy substituents, and the like; and n designates that sufficient R groups are provided to satisfy the remaining valencies of X, e.g., n is 3 and X is nitrogen when the electropositive complexing site is quaternary ammonium. In some cases, the stability of the electropositive complexing sites is enhanced when R is lower alkyl, especially methyl. It is also possible for X to be contained in a heterocyclic structure. Frequently, such cyclic structures contain 5 or 6 ring members with one or two members being the charge-carrying center X.

The electropositive complexing site may be bonded to the solid support through, for example, an alkylene, arylene, silyl or siloxy group.

Solid supports having electropositive complexing sites include inorganic substrates, such as carbon, silica gel, zeolite, clay and glass beads. These supports may have the electropositive complexing sites affixed through adsorption, reaction or graft polymerization. See, for instance, Japanese Kokai Nos. 50/32085 and 52/26386. See also, P. Tundo, et al., "Anion-Exchange Properties of Ammonium Salts Immobilized on Silica Gel," *J. Am. Chem. Soc.*, Vol. 104, pp 6547–6551 (1982), and P. Tundo, et al., "Phase Transfer Catalysts Immobilized and Adsorbed on Alumina and Silica Gel", *J. Am. Chem. Soc.*, Vol 104, pp 6551–6555 (1982). U.S. Pat. No. 4,430,496 discloses silyl alkylammonium sites on inert particles. See also German patent application No. 2,433,409. The above are all herein incorporated by reference.

Suitable supports for the electropositive complexing sites also include water-insoluble anionic resins. The resin can be varied to convenience and can comprise essentially any resinous composition. The resins include high molecular weight polymers and copolymers e.g., addition and condensation polymers, including polyalkylenes, polyesters, polycarbonates, polysulfones, polyimides, phenolic resins, formaldehyde resins, polyurethanes and the like, and the electropositive complexing sites may be adsorbed, reacted or grafted on the resin. While many available resins are carbon-based, silica-based resins may also find application in processes in accordance with this invention. These resins include organosiloxane polymers, such as dimethyl polysiloxane, methylphenyl polysiloxane, methylvinyl polysiloxane, cyanoalkylmethyl polysiloxanes and fluoroalkyl polysiloxanes. See, for example, U.S. Pat. No. 4,417,066, issued Nov. 22, 1983, pertaining to organosiloxane polymers containing quaternary ammoninum sites. U.S. Pat. No. 4,410,669 discloses polymeric ammonium compounds with a silica-type backbone which are said to exhibit good thermal stability and inertness to chemical attack. Both of these patents are herein incorporated by reference.

Monomers which can be employed in preparing carbon-based resins include styrene and styrene derivatives such as methylstyrene, ethylstyrene, vinylnaphthalene, 3,4,6-trimethylstyrene, chlorostyrene, methoxystyrene, N,N-dimethylaminostyrene, nitrostyrene, chlorostyrene, trifluorostyrene, trifluoromethylstyrene and aminostyrene; butadiene; acrylonitrile and acrylonitrile derivatives; acrylic acid and acrylates such as methyl acrylate and chloromethyl acrylate; methacrylic acid and methacrylates such as cyclohexyl methacrylate, dimethylaminoethyl methacrylate, glycidyl methacrylate and methyl methacrylate; maleates such as diethyl maleate; fumarates such diethyl fumarate; vinyl ketones such as methyl vinyl ketone and ethyl isopropyl ketone; vinylidenes; acrylamide and acrylamide derivatives; aliphatic acid vinyl esters such as vinyl acetate, vinyl butylate and vinyl caproate; formaldehyde with, e.g., phenol, xylene, urea, melamine; bisphenol A; sulfones such as dichlorodiphenyl sulfone; phosgene; toluene diisocyanate; polyols such as ethylene glycol; and epoxybutadiene; etc.

For purposes of strength and chemical resistance, the resin is preferably cross-linked. Representative resins which can be cross-linked include styrene-divinylbenzene, styrene-glycol dimethacrylate, aniline-formaldehyde, aryl polyamine-formaldehyde, phenol formaldehyde, polyacrylate, and the like. Generally, the amount of cross-linking agent provided is an amount of about 4 or 5 to 30 or 40 mole percent based on the monomer used to prepare the resin.

Cross-linking agents which can be employed in preparing resins include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl) ethylene diamine, diallyl phthalate, triallylamine, N,N'-ethylenediacrylamide, ethylene glycol dimethacrylate, triethylene glycol dimethacrylate, trimethylolpropane trimethacrylate, trimethylolpropane triacrylate, triallyl isocyanurate and diallyl melamine.

The resins can take many forms, such as swellable gels, semi-porous or iso-porous resins, or macro-porous (macro-reticular) resins. The resins may be spherical or irregular granules which in turn may be supported on a larger solid structure. Frequently, the major dimension of the resins is about 0.1 to 5 millimeters (e.g., 0.3 to 1 or 2 millimeters).

Anion exchange resins having quaternary amine sites and tertiary amine sites are commercially available. These resins include resins with acrylic matrices such as Amberlite (TM) IRA-68, IRA-60, and XE-258 resins available from Rohm & Haas Co.; phenolic-containing matrices such as Amberlite (TM) IRA-4B resin available from Rohm & Haas Co.; styrene-divinylbenzene matrices such as Amberlite (TM), IRA-900, IRA-904, IRA-93, IRA-94, and IRA-400 resins available from Rohm & Haas Co., Dowex (TM) 1, 2, 11, WGR, MSA-1, and MWA-1 resins available from the Dow Chemical Company, and Duolite (TM) A-101, A-102, and A-114, available from the Diamond Shamrock Corp.

Preferably, the support has at least about 0.1, e.g., 0.5 to 10, say 0.5 to 5 milli-equivalents of exchange capacity (based on the pendant electropositive complexing sites) per gram of dry support. It is at these sites that the association occurs between the metalate anion and the insoluble support.

The association of the metalate with the electropositive complexing sites on the insoluble support may be provided in any convenient manner. Usually the placing of the metalate on the insoluble support is accomplished by a loading technique whereby a soluble metalate salt is contacted in solution in an inert liquid medium with the insoluble support to displace original anion at the site.

The counter ions to the metalates useful in preparing the solid supported metalates used in this invention are preferably water-soluble, include alkali metals, alkaline earth metals, ammonium ion, copper, zinc, iron, quaternary ammonium cations, quaternary phosphonium cations, sulfonium cations, and other cations.

Inert liquid media often include water, aliphatic and aromatic hydrocarbons and substituted hydrocarbons such as hexane, benzene, toluene, xylene, o-dichlorobenzene, methylene chloride, chloroform, carbon tetrachloride, and the like.

The loading can occur at any temperature at which the metalate is dissolved. The temperature employed is preferably below that which results in unduly adverse effects to the reactants. Usually, the temperature will be about 0° C. to 120° C., say, about 15° C. to 100° C. Any convenient pressure may be employed, and subatmospheric pressures may assist in the dispersion of the metalate anion throughout the support. The loading process is typically conducted under a suitable atmosphere which frequently may be a substantially inert atmosphere, such as air or nitrogen, for a sufficient period of time to enable desired amounts of metalate anion to become associated with the electropositive complexing sites. This period of time will generally vary with the method, reagents and conditions employed, but it will often be about 0.5 to 50, say about 1 to 15 hours. The resulting product containing the metalate may be recovered by any convenient physical separation technique, such as filtering, decanting and evaporating.

In order to obtain the desired metalate in association with the electropositive complexing sites on the insoluble support, it is not necessary to use the metalate form. Indeed, any form of the metal which will yield the metalate by reaction subsequent to the loading, including in situ during the hydrolysis reaction, is believed to be suitable. The metal-containing anions may therefore contain halide, e.g., chloride and iodide; sulfide, aliphatic or aromatic hydrocarbon, or similar substituents. The selection of the metalate or precursor of the metalate will, in general, be dependent upon the availability of the compound and its processing characteristics in order to form the association with the electropositive complexing sites of the insoluble support and, in the case of the precursors to the metalate, additionally the ability to form the desired product.

Typically during loading, the mole ratio of metalate ion to the electropositive complexing sites is between about 1:100 to about 100:1, and frequently is between about 1:1 to 25:1. In the prepared product with the associated metalate anion, the ratio of electropositive complexing sites having associated metalate anion to total electropositive complexing sites is frequently between about 1:10 to 1:1, preferably about 0.9:1 to 1:1. It has generally been noted that even though the metalate anion may have a negative charge of two or more, such as molybdate and tungstate, the metalate anion may be associated with only one electropositive complexing site. Typically, the metalate loaded support comprises, as determined by conventional elemental analysis, at least about 0.1, and preferably at least about 1, often about 2 to 30, say, 5 to 25, weight percent of the metal of the metalate (metal basis) based on total weight of the dry support. The saturation of the electropositive complexing sites of the insoluble support is the only limitation upon the maximum weight percent of metalate contained in association with the electropositive complexing sites on the insoluble support. It is generally desired to achieve as close to saturation levels as possible for reasons of activity and life. Moreover, it is also believed that the association of the metalate anion with the electropositive complexing sites assists in stabilizing the electropositive complexing sites under hydrolysis conditions. This is particularly important when a decomposition of the electropositive complexing sites results in adverse effects to the desired alkylene glycol product. For instance, when using quaternary amine-containing anionic exchange resins, the degradation of the resin may yield amines which can provide an odor to the alkylene glycol product.

As disclosed in copending U.S. Serial No. 594,267, herein incorporated by reference, the stability of the electropositive complexing sites is believed to be enhanced by the addition of small quantities of metalate anion to the reaction mixture. This metalate anion is believed to replace any metalate anion lost from the electropositive complexing sites during the course of the reaction. Often, the amount of metalate anion provided can be relatively small, e.g., less than 1,000 ppm by weight based on the reactants fed to the reaction zone, say, about 1 to 1000, e.g., about 50 to 250, ppm by weight. Often, the mole ratio of metalate anion added to metalate anion in association with the electropositive complexing sites is less than 1:20, say 1:50 to 1:1000.

The metalate anion may be provided as any convenient, dissociatable metalate anion-containing material. Thus, the metalate anion-containing material is frequently a water-soluble acid or salt, i.e., the cations include hydrogen, alkali metals, alkaline earth metals, ammonium ion, copper, zinc, iron, quaternary ammonium cations, quaternary phosphonium cations, sulfonium cations, and the like. Conveniently, the cation is sodium or potassium due to its ready availability. However, in some instances it is desirable to employ an organic-containing cation to facilitate its separation from the alkylene glycol product by extraction into a water-immiscible phase in which it is preferentially soluble. See for further discussion U.S. patent application Ser. No. 594,266, filed on even date herewith, of B. T. Keen, et al., herein incorporated by reference. The recovery of metalate cations can also be effected by, say, an anion exchange solid such as disclosed in U.S. Ser. No. 594,269, herein incorporated by reference.

The metalate anion need not be the same as the metalate anion initially in association with the electropositive complexing sites; however, the initial metalate anion will tend to be replaced by the metalate anion added. Consequently, the metalate anion added is usually the same as the initial metalate anion.

In the case of catalyzed reactions, the catalyst is generally provided in an amount of at least 0.005 percent, based on the weight of the vicinal alkylene oxide employed, and is preferably employed in an amount between about 0.01 and about 90 percent by weight, and most preferably between about 0.05 and about 30 percent by weight, based on the weight of the alkylene oxide employed.

The production of alkylene glycol according to this invention is effectively carried out in the presence of a gas, such as air, carbon dioxide, argon or nitrogen, as a diluent for the reaction system. The very nature of the process generally provides carbon dioxide and nitrogen in the reaction system. The presence of carbon dioxide has been observed, in some instances, to decrease the selectivity to the monoethylene glycol product and, as a result, the presence of carbon dioxide is sometimes not preferred although some carbon dioxide will normally be present.

The adjustment of the pH of the reaction system may affect the rate and, importantly, selectivity to monoalkylene glycol. The pH should be maintained at a value of about 5 to 10, preferably 7 to 9, during the process. The adjustment of pH may be affected by a number of mechanisms. For instance, acid or base such as sulfuric acid, hydrochloric acid, phosphoric acid, carbonic acid, alkali metal hydroxide (e.g., sodium hydroxide and potassium hydroxide) or ammonium hydroxide may be added. Preferably, an adjuvant, which is used to modify the pH, does not unduly affect the reaction system or products.

The process is usually carried out at a temperature between about 20° C. and about 250° C., preferably between about 50° C. and about 200° C. Temperatures above 250° C. may be employed depending on the selection of the alkylene oxide, if the reaction is catalyzed and, if so, the catalyst employed and pressure employed; however, such high temperatures are not generally preferred.

The process is typically carried out at a pressure in the range between about 0 kg/cm$^2$G and about 1000 kg/cm$^2$G and preferably between about 2 kg/cm$^2$G and about 100 kg/cm$^2$G, although pressures outside these preferred ranges are believed to be operable.

The processes of this invention may be carried out as a batch reaction or as a continuous process. Conventional autoclaves can be employed when using elevated temperatures, but glassware-type equipment can be used when operated at moderate pressures. Plug-flow reactors are often utilized in conventional continuous procedures. Solvent may be recycled and catalyst may be recovered.

Use of the claimed process in a continuous process is particularly advantageous due to the low heat of vaporization of the alkylene glycol ether co-solvent relative to that of water. The distillation procedure which is typically employed for product recovery and recycle of the reaction solvent and reactants may therefore be conducted while realizing a considerable savings in energy.

The reaction may be carried out for periods of varied duration, e.g., fractions of a second or periods of hours. The process conditions are governed by the amounts of solvent and catalyst employed, the pressures and temperatures employed, and like considerations.

It has been observed that when the alkylene oxide is ethylene oxide, the selectivity to monoethylene glycol over diethylene glycol and triethylene glycol is greater than 70 molar percent and generally greater than 80 molar percent, preferably greater than 90 percent.

The following examples show various modes in the practice of this invention but are not intended to limit the invention. All parts and percentages of solids are by weight and of liquids and gases are by volume unless otherwise indicated.

EXAMPLES

Control A 68.0 g water and 1.6 g sodium molybdate were charged into a 300 cc stainless steel autoclave equipped with an automatic stirring device. 37.0 g ethylene oxide was then introduced into the reaction vessel under 60 psig of nitrogen gas. The temperature of the autoclave was then raised to 140°–150° C. for a period of 2.5 hours. It was noted that during the course of the hydrolysis reaction, the pressure within the vessel first increased and then decreased before finally stabilizing.

Analysis of the reaction products showed that 100% of the ethylene oxide was hydrolyzed. Monoethylene glycol selectivity as determined through use of the formula set forth immediately below was found to be 88.6%.

$$\text{MEG Selectivity} = \frac{\text{Wt \% MEG}}{\text{Wt \% MEG} + \text{Wt \% DEG} + \text{Wt \% TEG}}$$

TABLE I

AUTOCLAVE EO HYDROLYSIS RUNS WITH ADDED GLYME

| Examples | H$_2$O (g) | Glyme (g) | EO (g) | Na$_2$MoO$_4$ (g) | H$_2$O/EO Mole Ratio | Glyme/H$_2$O Wt. Ratio | Conc. Na$_2$MoO$_4$ Wt. % on EO | Temp. Range °C./Time Hr. | MEG Selectivity (%) |
|---|---|---|---|---|---|---|---|---|---|
| Cont. A | 68 | — | 37.0 | 1.6 | — | — | 4.8 | 140/150/2.5 | 88.6 |
| 1 | 54 | 54 | 32.5 | 0.83 | 4.0 | 1.0 | 2.5 | 130–140/3 | 90.0 |
| 2 | 18 | 90 | 32.0 | 0.83 | 1.4 | 5.0 | 2.5 | 130–160/2.5 | 92.8 |
| 3 | 27 | 54 | 33.0 | 0.83 | 2.0 | 2.0 | 2.5 | 130–140/1.6 | 92.2 |
| 4 | 54 | 27 | 65.8 | 1.6 | 2.0 | 0.5 | 2.5 | 140/1.5 | 87.4 |
| 5 | 54 | 27 | 22.0 | 0.56 | 6.0 | 0.5 | 2.5 | 130–140/1.2 | 90.8 |
| 6 | 27 | 54 | 28.5 | 0.28 | 2.3 | 2.0 | 1.0 | 130–145/1.5 | 94.3 |
| 7 | 27 | 54 | 10.7 | 0.29 | 6.0 | 2.0 | 2.5 | 135–145/1.5 | 95.3 |
| 8 | 20 | 61 | 12.1 | 0.31 | 4.0 | 3.0 | 2.5 | 140–155/2.5 | 94.9 |
| 9 | 20 | 61 | 33.0 | 0.83 | 1.5 | 3.0 | 2.5 | 130–150/2.5 | 87.0 |
| 10 | 41 | 41 | 12.5 | 0.32 | 8.0 | 1.0 | 2.5 | 145–150/1.3 | 93.5 |
| 11 | 20 | 61 | 8.25 | 0.21 | 5.9 | 3.0 | 2.5 | 145–150/2.0 | 96.0 (97+)* |
| 12 | 27 | 54 | 33.3 | 1.65 | 2.0 | 2.0 | 5.0 | 140–150/1.5 | 94.3 (99+)* |
| 13 | 27 | 54 | 8.2 | 0.21 | 8.1 | 2.0 | 2.5 | 140–150/1.6 | 95.0 (98+)* |

*EO Conversion Percent wherein: MEG = monoethylene glycol
DEG = diethylene glycol
TEG = triethylene glycol wherein:
MEG = monoethylene glycol
DEG = diethylene glycol
TEG = triethylene glycol

Example 1

54.0 g 1,2-dimethoxyethane, 54.0 g water and 0.83 g sodium molybdate were charged into a 300 cc stainless steel autoclave equipped with an automatic stirring device. 32.5 g ethylene oxide was then introduced into the reaction vessel under 60 psig of nitrogen gas. The temperature of the autoclave was then raised to 130°–140° C. for a period of three hours. It was noted that during the course of the hydrolysis reaction, the pressure within the vessel first increased and then decreased before finally stabilizing.

Analysis of the reaction products showed that 100% of the ethylene oxide was hydrolyzed. It was also noted that no decomposition of the dimethoxyethane was evident. Monoethylene glycol selectivity was found to be 90.8%.

Examples 2–13

The general procedure employed in Example 1 was repeated using various concentrations of water, 1,2-dimethoxyethane, ethylene oxide and molybdate-containing catalyst. The results of these runs, as well as those of Control A and Example 1, are set forth in Table I.

Example 14

75.0 g water, 1.50 g sodium molybdate and 25.0 g ethylene oxide were chilled in a 120 cc septum capped serium bottle. Ten cc of gaseous carbon dioxide was syringed into the stock solution and mixed. Three cc of the stock solution and 2.6 cc 1,2-dimethoxyethane were syringed into a 3.5-inch (0.5-inch od) stainless steel microreactor (volume = 8.0 cc). The reactors were sealed with 0.5-inch swagelock caps. The reaction was run by shaking the microreactor in a constant temperature oil bath at 180° C. Ethylene oxide conversion was 100 percent and monoethylene glycol selectivity was 96.56 percent.

Examples 15–41

Examples 15 through 41 were run in like fashion to Example 14 with resultant weight percent of sodium molybdate, weight ratio of water to ethylene oxide, weight ratio of 1,2-dimethoxyethane to ethylene oxide, presence or absence of carbon dioxide, temperature °C. and MEG selectivity as listed in Table II. Ethylene oxide conversion was 100 percent except where noted. Reaction time was approximately 2.5 hours in all cases. Total reagent volume was approximately 6.0 cc in all cases.

Comparative Examples B–G

Examples of catalyzed runs where no alkylene glycol ether co-solvent was employed were conducted as in Examples 14–51. The results of these runs are set forth in Table II.

TABLE II

Microreactor EO Hydrolysis Runs with Added Glyme

| Example Number | Sodium Molybdate Wt % on EO | H$_2$O/EO Wt Ratio | Glyme/EO Wt Ratio | Bath Temp Degrees C. | CO$_2$ | MEG Selectivity |
|---|---|---|---|---|---|---|
| 14 | 6 | 3 | 9.0 | 180 | Yes | 96.56 |
| 15 | 6 | 3 | 3.0 | 180 | No | 96.23 |
| 16 | 6 | 3 | 3.0 | 150 | Yes | 95.79 |
| 17 | 6 | 1 | 1.0 | 180 | Yes | 92.70 |
| 18 | 6 | 1 | 1.0 | 150 | No | 91.53 |
| 19 | 2 | 3 | 9.0 | 180 | No | 94.67 |
| 20 | 2 | 3 | 3.0 | 180 | Yes | 92.20 |
| 21 | 2 | 3 | 3.0 | 150 | No | 91.50 |
| 22 | 2 | 1 | 3.0 | 180 | Yes | 90.53 |
| 23 | 2 | 1 | 1.0 | 180 | No | 89.66 |
| 24 | 2 | 1 | 1.0 | 150 | Yes | 88.77 |

TABLE II-continued

Microreactor EO Hydrolysis Runs with Added Glyme

| | Sodium Molybdate Wt % on EO | H₂O/EO Wt Ratio | Glyme/EO Wt Ratio | Bath Temp Degrees C. | CO₂ | MEG Selectivity |
|---|---|---|---|---|---|---|
| 25 | 6 | 5 | 5.0 | 180 | No | 96.44 |
| 26 | 6 | 5 | 5.0 | 150 | Yes | 96.10 |
| 27 | 2 | 5 | 0.0 | 180 | No | 90.73 |
| 28 | 2 | 5 | 0.0 | 150 | Yes | 89.91 |
| 29 | 2 | 5 | 5.0 | 180 | Yes | 93.27 |
| 30 | 2 | 5 | 5.0 | 150 | No | 93.05 |
| 31 | 6 | 5 | 2.2 | 150 | Yes | 95.30 |
| 32 | 2 | 5 | 2.2 | 150 | Yes | 91.98 |
| 33 | 6 | 1 | 6.0 | 180 | No | 94.65 |
| 34 | 2 | 1 | 3.0 | 180 | No | 89.05 |
| 35 | 2 | 1 | 6.0 | 180 | No | 94.09 |
| 36 | 6 | 3 | 6.0 | 180 | No | 95.45 |
| 37 | 2 | 3 | 6.0 | 180 | No | 93.71 |
| 38 | 6 | 3 | 9.0 | 150 | No | 95.77 (88)* |
| 39 | 6 | 1 | 3.0 | 150 | Yes | 91.86 (92)* |
| 40 | 2 | 3 | 9.0 | 150 | Yes | 95.40 (83)* |
| 41 | 2 | 1 | 3.0 | 150 | No | 90.54 (90)* |
| Comparative Examples | | | | | | |
| B | 6 | 3 | | 180 | Yes | 92.48 |
| C | 2 | 3 | | 180 | Yes | 87.62 |
| D | 6 | 1 | | 180 | Yes | 86.50 |
| E | 2 | 1 | | 180 | Yes | 79.31 |
| F | 6 | 3 | | 150 | Yes | 92.08 |
| G | 2 | 3 | | 150 | Yes | 87.13 |
| H | 6 | 1 | | 150 | Yes | 87.94 |
| I | 2 | 1 | | 150 | Yes | 83.26 |
| J | 6 | 5 | | 180 | Yes | 94.03 |
| K | 6 | 5 | | 150 | No | 91.54 |
| L | 2 | 2 | | 150 | No | 83.6 |
| M | 8 | 2 | | 150 | No | 90.3 |
| N | 2 | 5.9 | | 150 | No | 89.9 |
| O | 2 | 10.0 | | 150 | No | 93.0 |
| P | 2 | 0.68 | | 150 | No | 70.5 |
| Q | 2 | 2.0 | | 150 | Yes | 85.5 |

*EO Conversion Percent

Examples 42–47

A 300 cc autoclave equipped with an automatic stirrer was charged with water, ethylene oxide and 1,2-dimethoxyethane in the weight ratios set forth in the following table. No catalysts were introduced into the system.

The internal temperature of the autoclave was elevated to 195° C. for a period of 2.5 hours. The reaction products were then analyzed to determine the selectivity of the reaction towards the production of monoethylene glycol. The results are set forth below.

| Example | Water:Glyme:Ethylene Oxide | MEG Selectivity (%) |
|---|---|---|
| 42 | 11:0:1 | 92.8 |
| 43 | 11:1:1 | 93.5 |
| 44 | 11:3:1 | 94.1 |
| 45 | 11:5:1 | 94.5 |
| 46 | 9:2:1 | 92.7 |
| 47 | 7:4:1 | 91.8 |

Examples 48–51

The procedure set forth in Examples 45–47 was repeated except that the temperature was maintained at 150° C. The weight ratios of reactants and the reaction results are set forth below.

| Example | Water:Glyme:Ethylene Oxide | MEG Selectivity (%) |
|---|---|---|
| 48 | 2.05:0:1 | 72.6 |
| 49 | 2.05:2.05:1 | 78.3 |
| 50 | 2.05:4.10:1 | 83.2 |
| 51 | 6.3:6.3:1 | 92.2 |

The following Examples demonstrate the use of the instant invention in association with reactions catalyzed with metalate impregnated ion exchange resins.

Example 52

To 25.0 grams DOWEX MSA-1 (TM) (The Dow Chemical Company) strongly basic anion exchange resin with quaternary ammonium functionality (20 to 50 mesh, chloride form, exchange capacity of 4.0 meg./g dry) were added 800 grams of 3.0 wt. % sodium molybdate ($Na_2MO_4$) aqueous solution to form a slurry. After stirring the slurry for 2 hours at room temperature, the liquid phase was decanted. The resin was washed with 500 milliliters of water twice. The resin was then slurried with 200 grams of a 3 wt. % sodium molybdate aqueous solution and charged to a 0.5 inch (1.27 cm) (id)×20 inch (50.8 cm) ion exchange column. A total of 2000 grams of 3 wt. % sodium molybdate aqueous solution was passed through the resin followed by 2 liters of distilled water. One liter of hot water (50–75° C.) was then passed through the resin. The resin was then vacuum filtered.

The following experiments were then carried out in a U-shaped ⅜" (0.95 cm) (outside diameter) stainless steel reactor. Generally, the reactor was charged from both ends with the desired volume of resin as a slurry in water. The volume of wet resin charged to the reactor as well as the reactor length are as listed in Table 1. The resin was held in place by stainless steel frits placed at each end of the bed. Chilled (5° C.) water and ethylene oxide (and alkali metalate when employed) were charged into a feed tank (internal volume 900 cc) and kept pressurized at 25 pounds per inch gauge (about 2.7 atmospheres absolute) with nitrogen. Stainless steel tubing (1/16") (0.16 cm) carried the reactants from the feed tank to the reactor and the products from the reactor to the product receiver. A back pressure regulator was used to keep the system pressure at about 13 atmospheres (200 pounds per sguare inch) gauge (nitrogen). The flow of reactants to the reactor was controlled by a dual piston high pressure liquid chromatography pump. The reaction products were cooled to ambient temperature by immersing a coiled section of a reactor exit line in a water bath. The U-shaped reactor was immersed (typically only to the level of the resin in the reactor) in a stirred constant temperature oil bath.

Conversion of the alkylene oxide was substantially 100 percent except where noted and monoalkylene glycol selectivities are as shown in Table 1. The anion exchange resin catalysts were prepared using aqueous solutions of the designated alkali metal metalate. In all instances, the chloride concentration of the wash effluent after the exchange with the metalate anion was less than about 5 ppm as determined by ion chromatography. The general procedure was to suspend the resin in an aqueous solution of the metalate (about 5 wt. %) at room temperature with stirring for about one-half hour, wash and then repeat contact with the metalate by eluting an aqueous solution of the metalate through a glass column packed with the resin until the chloride was virtually completely exchanged. The resin was then washed thoroughly with water.

The below described analytical method was used to determine alkylene glycol products in samples from reaction effluents. The samples were prepared by adding about 2 weight percent 1,3-butanediol as an internal standard. Approximately 50 microliters of this admixture were added to 1.0 milliliter of Regisil (TM) silane, i.e., (BSTFA) N,N -bis trimethylsilyl trifluoroacetamide, available from the Regis Chemical Company, Morton Grove, Illinois, in a serum vial and mixed for at least about 12 hours. The weight percent monoethylene glycol, diethylene glycol and triethylene glycol were determined by standard vapor phase chromatography using a Hewlett Packard 5880 (TM) gas chromatograph equipped with a 4 meter by ⅛ inch (0.32 centimeter) (outside diameter) stainless steel column packed with 20 percent OV -101 methyl silicone stationary liquid phase supported on 80-100 mesh Chromosorb W HP (TM) available from Supelco, Inc., Bellefonte, Pa. The selectivity to each glycol component is calculated as the quotient of the weight percent of the subject glycol divided by the sum of the weight percents of each of monoethylene glycol, diethylene glycol and triethylene glycol.

TABLE 1

| Ex. | Ethylene Oxide/Wt. % | Water (Wt. %) | Alkali Metal-ate/PPM wt. | Resin Type/ Metalate Loaded | Volume Wet Resin in Reactor (cc) | Approximate Reactor Length (centi.) | Flow Rate ml/min. | Reaction Temp. °C. | Mono Alkylene Glycol Selectivity % |
|---|---|---|---|---|---|---|---|---|---|
| Ex. 52 | 9.1 | 90.9 | None | DOWEX MSA-1 /MoO$_4^{-2}$ | 20 | 43 | 1.5 | 130 | 98.7 |

Examples 53

The procedure of Example 52 was basically repeated except (1) 1,2-dimethoxyethane was added as a co solvent, and (2) the hydrolysis ratio was 9:1. Moreover, the flow rate was reduced to 0.8 ml/minute. The specific reaction conditions and feed stream composition are set forth below.

| Reaction Conditions | Feed Composition | |
|---|---|---|
| Flow rate: 0.8 ml/min. | Deionized water (g) | 360.08 |
| Pressure: 200 psig | 1,2 dimethoxy ethane (g) | 40.0 |
| Temperature: 130° C. | Ethylene oxide | 40.0 |
| Hydrolysis ratio: 9:1 | | |

The results from this experimental run are set forth below.

| | REACTANT SOLUTION | | | Resin Type/ Metalate Loaded | Volume Wet Resin in Reactor (cc) | Approximate Reactor Length (centi.) | Flow Rate ml/min. | Reaction Temp. °C. | Mono Alkylene Glycol Selectivity % |
|---|---|---|---|---|---|---|---|---|---|
| Ex. | Ethylene Oxide/Wt. % | Water (Wt. %) | 1,2 dimethoxy-ethane (wt. %) | | | | | | |
| 53 | 9.09 | 81.82 | 9.09 | DOWEX MSA-1/ MoO$_4^{-2}$ | 20 | 43 | 0.8 | 130 | 98.93 |

It is claimed:

1. A process for the selective production of monoalkylene glycol comprising reacting in a liquid phase in the presence of a water-soluble metalate anion catalyst, a vicinal alkylene oxide of the formula:

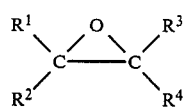

wherein $R^1$, $R^2$, $R^3$ and $R^4$ each designate a hydrogen atom, an alkyl group having between 1 and about 10 carbon atoms, and aryl group having at least 6 carbon atoms, an alkenyl group having 2 or 3 carbon atoms or a cycloalkyl group having 3 to 6 carbon atoms, with water in an aqueous medium comprising a water miscible ethylene glycol ether co-solvent of the formula:

R(OCH$_2$CH$_2$)$_n$OR wherin R is $C_1$-$C_4$ alkyl and n is a whole number ranging from about 1 to about 10, said co-solvent being present in amounts ranging from about 5 to about 85 wt. % based upon the total weight of water and co-solvent.

2. The process of cliam 1 wherein the water miscible co-solvent is present in amounts from about 15 to 75 wt. %.

3. The process of claim 1 wherein the water miscible co-solvent is present in amounts from about 30 to 60 wt. %.

4. The process of claim 1 wherein the organic solvent is 1,2-dimethoxyethane.

5. The process of claim 4 wherein 1,2-dimethoxyethane is present in amounts ranging from 30 to 60 wt. % based upon the weight of the liquid medium.

6. The process of claim 2 wherein the molar ratio of water to alkylene oxide is from about 1:1 to about 10:1

7. The process of claim 1 wherein the catalyst is selected from the group consisting of sodium molybdate, potassium molybdate and lithium molybdate.

8. The process of claim 1 wherein the catalyst is impregnated in an ion exchange resin.

9. A process for the production of ethylene glycol through the hydrolysis of alkylene oxide at a temperature of between about 20° C. and about 250° C. and a pressure of about 0 kg/cm$^2$ and about 1,000 kg/cm$^2$, comprising conducting said reaction in an aqueous medium containing from 15 to 75 wt % of 1,2-dimethoxyethane based upon the total weight of water plus 1,2-dimethoxyethane so as to inhibit the formation of polyethylene glycols.

* * * * *